United States Patent [19]

Lower

[11] Patent Number: 4,640,271
[45] Date of Patent: Feb. 3, 1987

[54] BONE SCREW
[75] Inventor: Jerry L. Lower, Bourbon, Ind.
[73] Assignee: Zimmer, Inc., Warsaw, Ind.
[21] Appl. No.: 795,963
[22] Filed: Nov. 7, 1985
[51] Int. Cl.$^4$ .............................................. A61F 5/04
[52] U.S. Cl. ............................. 128/92 YF; 128/92 YE
[58] Field of Search ....................... 128/92 YF, 92 YE

[56] References Cited

U.S. PATENT DOCUMENTS

| | | | |
|---|---|---|---|
| 2,511,051 | 6/1950 | Dzus | 128/92 YF |
| 3,051,169 | 8/1962 | Grath | 128/92 |
| 3,842,824 | 10/1974 | Neufeld | 128/92 BA |
| 3,892,232 | 7/1975 | Neufeld | 128/92 BA |
| 4,175,555 | 11/1979 | Herbert | 128/92 B |
| 4,383,527 | 5/1983 | Asnis et al. | 128/92 EB |
| 4,450,835 | 5/1984 | Asnis et al. | 128/92 EB |
| 4,456,005 | 6/1984 | Lichty | 128/92 YF |
| 4,463,753 | 8/1984 | Gustilo | 128/92 B |
| 4,530,355 | 7/1985 | Griggs | 128/92 BB |

FOREIGN PATENT DOCUMENTS 2108229  5/1983  United Kingdom .

OTHER PUBLICATIONS

Mecron ® Cannulated Cancellous Screws—advertisement, *JBJS*, Dec. 1983—65-A—Mecron Med. Products, Inc.
Howmedica ® The Asnis Guided Screw System Brochure & Surgical Technique © Howmedica, Inc., 1981—Howmedica, Inc.
Richards ® Cannulated Hip Pin Brochure © Richards Medical Company, 1984.
"Hip Nails for All Occasions" Raymond G. Tronzo, M.D.—Orthopedic Clinics of North America—vol. 5, No. 3, Jul. 1974—pp. 479–491.

Primary Examiner—John J. Wilson
Assistant Examiner—C. W. Shedd
Attorney, Agent, or Firm—Margaret L. Geringer

[57] ABSTRACT

A bone screw comprising a shaft having a first set of leading threads and a second set of trailing threads spaced apart from the first set of threads by an unthreaded central portion. The second set of threads are carried externally on a sleeve having a smooth inner cylindrical surface such that the sleeve is slidable about the unthreaded shaft portion. A raised lip is provided about the trailing end of the shaft to retain the sleeve on the shaft.

The first and second set of screw threads are like-handed, but preferably of different pitch, with the pitch of the first set of screw threads exceeding that of the second set of screw threads to effectively hold portions of a fractured bone in compressive engagement.

Provision of the second set of threads on a slidable sleeve enables the main shaft to slide through the sleeve and back out of the bone, when absorption occurs such as when the invention is used to repair a femoral neck fracture. The ability of the main shaft to back out in a direction opposite the femoral head is an advantage because if the second set of threads were fixed on the main shaft, the bone screw would tend to penetrate the femoral head and enter the joint capsule when absorption occurs, which would cause interference of the joint articulation and pain to the patient.

10 Claims, 7 Drawing Figures

BONE SCREW

BACKGROUND OF THE INVENTION

This invention generally relates to a bone screw for surgically fastening fractured or severed bone fragments. This invention is particularly suitable for use as a hip fixation pin for fractures of the neck of the femur, although is not limited thereto.

The present invention utilizes many of the features of U.S. Pat. No. 4,175,555 to Herbert which discloses a bone screw having screw threads which are like-handed but of different pitch on its respective leading and trailing ends and spaced apart by a smooth, cylindrical shaft. The pitch of the leading threads may exceed that of the trailing threads in order to hold the bone fragments in compressive engagement.

U.S. Pat. No. 3,051,169 to Grath provides a bone screw disclosed as suitable for use with femoral neck fractures which also includes a first leading set of threads and a second trailing set of threads which are indicated to be preferably of the same pitch. The second set of threads is carried on a sleeve member which fits snugly around the unthreaded shaft at its inner end, but then for the remainder of the sleeve's length has a somewhat larger internal diameter to accommodate a helical spring between the sleeve and the shaft of the screw. The sleeve carries a spacing ring to center the sleeve on the shaft. Outside of the ring is another helical spring which is supported against a nut threadably adjustable on the outer threaded end of the screw shaft. The disclosure states that by use of the spring means, the broken bones are forced together to facilitate and expedite healing.

It is also known to use hip screws which include only one set of threads on an elongated shaft. Such a screw is often utilized in a multiple pinning technique, i.e., two or three such screws all being aligned through the head and neck of the femur for fixation of a neck fracture. Examples of such pins are illustrated and disclosed in U.S. Pat. Nos. 3,842,824 and 3,892,232 to Neufeld and U.S. Pat. Nos. 4,383,527 and 4,450,835 to Asnis.

Another type of fixation device commonly utilized for fractures of the femoral neck, is a compression hip screw which typically includes a first angled barrel and plate member and a lag screw member receivable within the barrel. An example of such a compression hip screw is shown in U.S. Pat. No. 4,530,355 to Griggs. Griggs also includes a compression screw which may be inserted through the barrel and threaded into the back portion of the lag screw to obtain a tight compression between the lag screw and the plate/barrel member. Once the desired amount of compression has been achieved, the compression screw may be removed or left in place at the option of the surgeon. In the course of time, absorption takes place near the fractured bone surfaces. Internal forces act on the lag screw/compression screw assembly, causing it to back out of the barrel, and thus protrude beyond the barrel/plate assembly. If the compression screw has been removed, absorption will still cause the lag screw to back out, but it is less likely to protrude as far out of the barrel/plate assembly. Such a compression hip assembly as described above, permits longitudinal sliding movement between the lag screw and the barrel due to the forces produced while such absorption occurs. Griggs also provides a clip which may be optionally insertable into the barrel to prevent axial rotation of the lag screw with respect to the barrel member.

It is noted that while a bone screw such as that described in the previously discussed U.S. Pat. No. 4,175,555 to Herbert is very suitable for fractures such as of the scaphoid and other similar small bones, if such a screw were used to achieve compression of a fracture across a femoral neck, absorption could cause the screw to protrude through the femoral head and into the joint capsule which would cause pain to the patient. The device would protrude into the joint capsule as a result of the absorption because as the bone shortens, it is unable to longitudinally slide out the other end as with the compression hip screw of Griggs.

OBJECTS OF THE INVENTION

A principle object of this invention is to provide a bone screw with a first set of fixed threads and second set of threads provided on a slidable sleeve to be spaced apart from the first set of threads.

Another object of this invention is to provide a simple bone screw especially suitable for use in femoral neck fractures which is to be used without a barrel/plate assembly, and yet which is still able to provide compression at the fracture site without the additional complications of springs or other complicated additional loading mechanisms, and yet which still provides for longitudinal sliding to enable adjustment when absorption occurs.

SUMMARY OF THE INVENTION

The present invention provides a bone screw including a first set of fixed threads at its leading end and a second set of threads at its trailing end spaced from the first set by a smooth cylindrical shaft. The first and second set of threads are like-handed, but of different pitch. The pitch of the first set of threads is preferably greater than that of the second set of threads in order to effect compression of the bone fragments about the fracture site. The second set of threads is provided on a sleeve which is freely slideable on the unthreaded shaft which is particularly advantageous for use as a hip screw so that the shaft is able to longitudinally slide within the sleeve to enable adjustment of the bone screw when absorption occurs due to the internal forces on the femoral bone joint. The ability of the shaft to longitudinally slide or back out through the externally threaded sleeve helps to prevent the bone screw from penetrating into the joint capsule when absorption occurs. The inner cylindrical surface of the sleeve has a uniform diameter throughout to provide an uninterrupted, smooth surface to directly slide against the smooth, unthreaded portion of the shaft. This interface enables the longitudinal sliding to occur. Axial rotation also may occur between the sleeve and the unthreaded shaft.

BRIEF DESCRIPTION OF THE DRAWINGS

These features and objects of the invention as well as others, will become apparent to those skilled in the art by referring to the accompanying drawings.

DETAILED DESCRIPTION OF THE INVENTION

Figure 1:
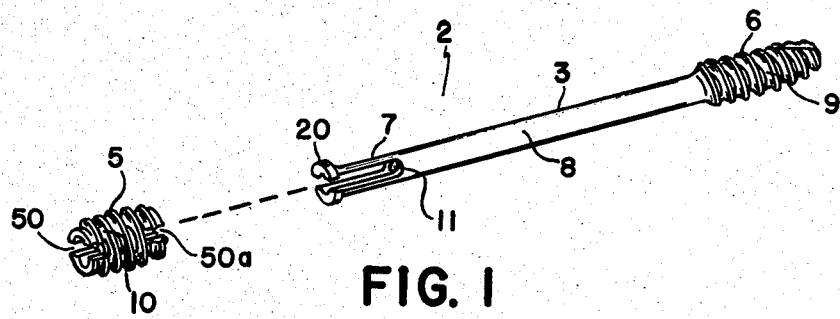
FIG. 1 is an exploded perspective view of a bone screw according to the present invention.

FIGS. 1-7 illustrate a particularly advantageous embodiment of the bone screw 1 of the present invention. The bone screw 1 is particularly suitable for and will be described in reference to a hip screw for fixation of fracture of the femoral neck area, although it is not limited to such usage.

The bone screw 1 includes a main shaft 2 and a separate sleeve member 5. The shaft 2 comprising a leading end portion 6 and an elongated, smooth unthreaded shaft portion 3. The leading end portion 6 includes a first set of uniformly pitched threads 9. The unthreaded shaft portion 3 is substantially cylindrical and includes a central portion 8 and a trailing end portion 7. The sleeve member 5 surrounds the unthreaded shaft portion 3 and is freely slidable thereabout. The sleeve member 5 has a smooth inner cylindrical surface 51. The sleeve member 5 includes a second set of uniformly pitched threads 10 externally thereon. The sleeve member 5 is typically positioned on or about the trailing end portion 7, spaced apart from the first set of threads 9 by the central portion 8. The outside diameter of the second set of threads 10 is preferably larger than the outside diameter of the first set of threads 9.

A protruding lip 20 is provided to prevent the sleeve member 5 from sliding off the unthreaded shaft portion 3. It is understood that alternate retaining means other than the protruding lip 20 could be provided.

A suitable driving means is provided on the trailing end portion 7 to accommodate a suitable tool 30 for driving the bone screw 1. The driving means may include a first transverse slot 11 in the trailing end 7 for accepting the corresponding narrow screw driving protrusion 31 on tool 30. The sleeve 5 may additionally have a second transverse slot 50 for accepting the corresponding wider screw driving protrusion 32 on tool 30. The screw may be inserted or driven with protrusion 31 engaged with slot 11 when slot 11 is not aligned with slot 50 as in FIG. 4, or both protrusions 31 and 32 may be engaged with slots 11 and 50 respectively when slots 11 and 50 are aligned as in FIG. 2. However, any suitable driving means and corresponding driving tool may be used with the present invention. It is noted that the bone screw 1 does not provide a conventional head on the trailing end, so that the trailing end can be wholly sunken into the bone into which it is inserted.

The first and second sets of threads 9 and 10 are like-handed but of different pitch. The pitch of the first threads 9 is preferably greater than that of the second threads 10 in order to provide a bone screw 1 which will simply achieve compression of the bone fragments upon insertion of the bone screw 1. The bone screw 1 may also be provided with a cannulation 16 throughout main shaft 2 to enable the bone screw 1 to be inserted over a guide wire 45 by the surgeon. Such guide wires 45 are well known in the art.

Figures 3, 5:
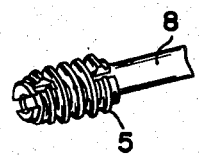
FIG. 3 is an end view of the bone screw of FIG. 2.
FIG. 5 is a cross-sectional view of the trailing end taken along lines 5—5 of FIG. 3.

As shown in FIG. 5, the inner cylindrical surface 51 of the sleeve 5 has a uniform diameter throughout and provides an uninterrupted smooth surface to directly interface with or slide against the smooth unthreaded portion 3 of the main shaft 2.

Figure 6:
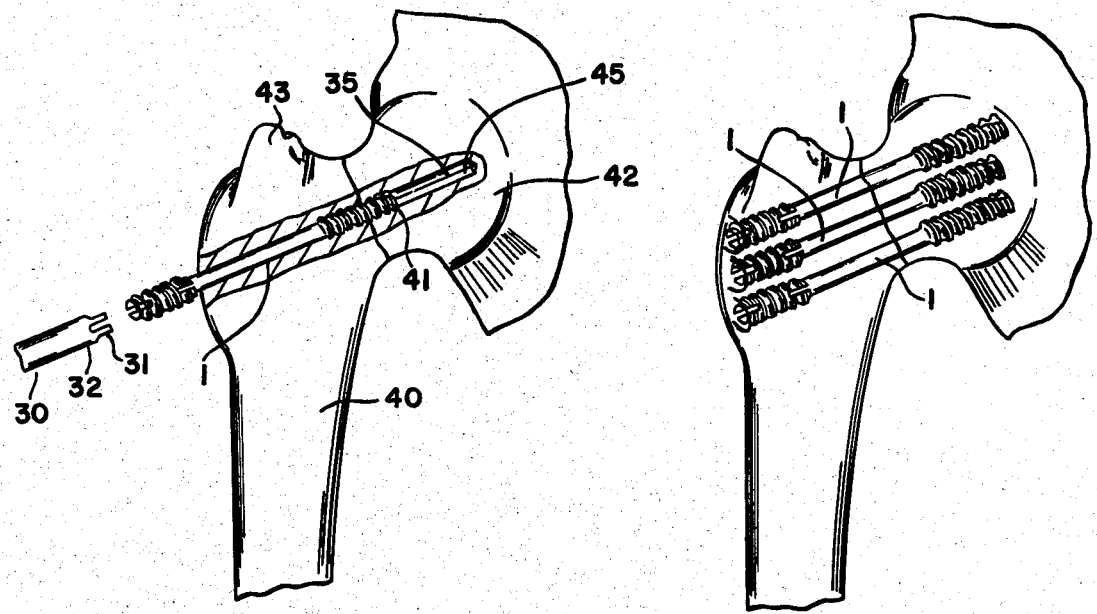
FIG. 6 illustrates the upper part of the femur in partial section with a partially inserted bone screw according to the present invention.
Figure 7:
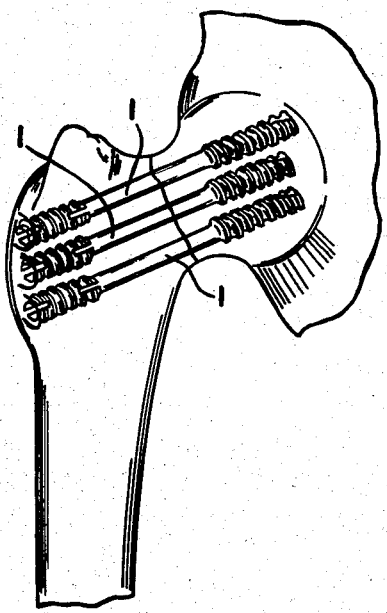
FIG. 7 illustrates the upper part of the femur with three fully inserted bone screws according to the present invention.

The bone screw 1 is utilized as a fixation device to connect portions of bone across a fracture therebetween. As shown in FIGS. 6 and 7, the bone screw 1 is utilized as a hip screw in the upper part of a femur 40 to connect the ball head portion 42 to the main portion of the femur which has been fractured across the neck 43 at fracture 41.

The bone screw 1 may be manufactured from such materials as titanium, titanium alloys or 316 LVM stainless steel, although other suitable biocompatible materials could be utilized. The first set of threads 9 are formed on an elongated piece of round cannulated stock and the smooth unthreaded portion 3 turned to size, leaving the raised lip 20 on the trailing end 7. The slot 11 is then formed in the trailing end 7.

The main shaft 2 may be provided in numerous lengths conveniently ranging from about 140 mm (5.5 in) to 60 mm (2.4 in). The preferred outer diameter of the unthreaded shaft portion 3 may be approximately 5 mm (0.197 in), with the raised lip 20 having about a 6 mm (0.24 in) diameter and a width of about 1 mm (0.04 in). The cannulation 16 may be approximately 3 mm (0.12 in) to readily fit over a 2 to 3 mm (0.08 to 0.12 in) guide wire 35. The inner diameter of the sleeve 5 is approximately 5.1 mm (0.2 in) to enable the unthreaded portion to readily slide on the unthreaded shaft portion 3, but without being too loose. The sleeve 5 may be approximately 25 mm (1 in) in length. The second set of threads 10 are formed on the tubular stock of the sleeve 5, and a slot 50 is cut thereon. The second set of threads 10 are formed to cut in both the forward and reverse directions. A slot 50a may also be formed on the leading edge of the sleeve 5. With slots 50 and 50a on the sleeve 5, this enables the sleeve 5 to be installed on the unthreaded shaft portion 3 without worrying about which end was the trailing end or the leading end of the sleeve 5 because the sleeve 5 could be put on either way. The sleeve 5 is installed by mechanically pressing the slot 11 on the trailing end 7 partially closed and forcing the sleeve 5 over the lip 20. When the pressure is released the sleeve 5 will be retained on the unthreaded shaft portion 3.

The thread form of the first set of threads 9 may be defined as a cancellous thread, preferably with a self-tapping design feature, while the thread form of the second set of threads 10 may be defined as a cortical thread form, preferably with a self-tapping design feature. Slots 50 and 50a eliminate the need for separate self-tapping cutting flutes on the sleeve 5.

In using the bone screw 1 of the present invention, it is first necessary to select the appropriate screw length desired. It is noted that the bone screw 1 is suitable for use in a multiple hip pinning technique as is known in the art. Thus, the insertion technique will be described herein for insertion of three bone screws 1 with reference to FIGS. 6 and 7. However, it is noted that single or multiple screw fixation may be utilized with the bone screw 1 of the present invention. However, if a single screw 1 is used, it may require larger dimensioning for added strength than that described previously, in particular for the diameter of the shaft and threads.

Figure 2:
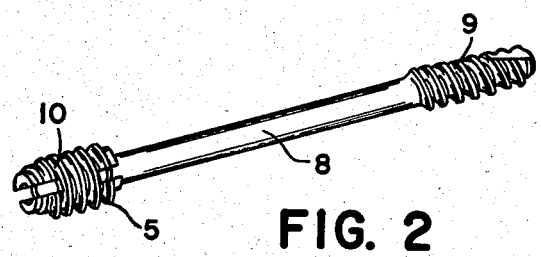
FIG. 2 is an assembled perspective view of the bone screw of FIG. 1.
Figure 4:
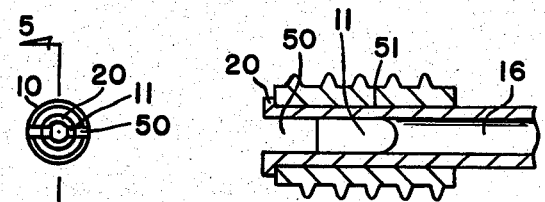
FIG. 4 is a partial perspective view of the trailing end of the bone screw of FIG. 2.

For multiple hip pinning, drill the main hole 45 according to conventional techniques. Insert the first set of threads 9 on the leading end 6 over a guide pin 35 via the cannulation 16 in the main shaft 2. A suitable screw-driving tool 30 is utilized to drive the bone screw 1 into the femur 40. Screw in the bone screw 1 until the threaded sleeve 5 tightens against the cortex of the femur 40 as shown in FIG. 6. Repeat this step for the other two bone screws 1. The femur 40 should be reduced by the surgeon at this point with a small gap between the fragments. The slot 50 in the sleeve 5 can be matched or lined up with the slot 11 in the trailing end 7 to drive both the sleeve 5 and the main shaft 2 as shown in FIG. 2, but this is not necessary. The tool 30 may be inserted into only the slot 11 when not aligned with slot 50 as shown in FIG. 4 upon insertion of the bone screw 1. A guide tool (not shown) may be used to align the screws 1 for insertion of multiple screws 1.

Continue to tighten the screws 1 in a pattern sequence to reduce the fracture 41 evenly. Even if the sleeve slot 50 is not engaged with the insertion tool 30, the second set of threads 10 will begin to rotate with the main shaft 2 due to the pressure and friction of the bone against the sleeve 5. Since the pitch of the leading threads 9 is greater than that of the trailing threads 10, compression of the bone fragments will occur, closing the gap at the fracture 41 and compressing the fragments together in secure engagement. FIG. 7 illustrates the three fully inserted bone screws 1 across the fractured neck 43 of a femur 40.

Once healing begins to occur and forces begin to act on the hip joint, absorption of the bone may occur effectively causing a shortening of the bone at the neck 43. Since the smooth inner diameter of the sleeve 5 is not engaged to the unthreaded shaft 3, when this shortening occurs, the forces on the femur cause the shaft 3 to slide through the sleeve 5. This may cause the trailing end 7 to slightly protrude out of the femur 40, but this is desirable rather than having the absorption cause the screw 1 to penetrate through the head 42 and into the joint capsule which would occur if the second threads 10 were not longitudinally slidable on the unthreaded shaft portion 3. The penetration into the joint capsule is not desirable because it would interfere with the joint articulation and cause pain.

When the surgeon has determined that healing of the fracture 41 is complete, the screws 1 may be removed. The main shaft portion 2 of the screw should be screwed out with an appropriate tool 30. The sleeve 5 may stay in the femur 40 at this point or be rotated out with the shaft 2. Screw out the shaft 2 until there is room to remove the sleeve 5. When there is room, screw the sleeve 5 out on the unthreaded shaft portion 3 by utilizing both the slots 11 and slots 50. Then finish removing the main shaft 2 from the femur 40.

The invention described herein is a bone screw 1, particularly suited for femoral neck fractures, which incorporates two sets of spaced apart screw threads 9 and 10, the second set 10 being provided on the trailing end 7 of the screw 1 on a slidable sleeve member 5 to allow the unthreaded shaft portion 3 of the screw to slide through the sleeve and back out of the femur in a direction opposite the head 42 of the femur when absorption occurs during the healing process. While this invention has been described and exemplified in terms of a particularly advantageous embodiment, those skilled in the art can appreciate that modifications can be made without departing from the spirit and scope of this invention.

I claim:
1. A bone screw for connecting portions of bone across a fracture therebetween, comprising:
    (a) a shaft comprising a leading end portion including a first set of uniformly pitched screw threads and an elongated, smooth unthreaded portion including a central portion and a trailing end portion;
    (b) a sleeve member having a smooth inner cylindrical surface surrounding the elongated unthreaded portion and being freely slidable thereabout, the sleeve member including a second set of uniformly pitched screw threads thereon, the sleeve member adapted to be positioned substantially about the trailing end portion spaced apart from the first set of threads by the central portion;
    (c) a retaining means to prevent the sleeve member from sliding off the shaft; and
    (d) a driving means on the trailing end portion to accommodate a tool for driving the screw.
2. The bone screw of claim 1 wherein the first and second sets of screw threads are like-handed but of different pitch.
3. The bone screw of claim 2 wherein the pitch of said first set of screw threads is greater than that of the second set of screw threads.
4. The bone screw of claim 1 wherein the retaining means includes a protruding lip about the trailing end of the shaft.
5. The bone screw of claim 1 wherein the shaft has a cannulation throughout its axial length.
6. The bone screw of claim 1 wherein the driving means includes a slot in the trailing end of the shaft for accepting a tool.
7. The bone screw of claim 6 wherein the driving means further includes a slot in the sleeve member.
8. The bone screw of claim 6 wherein the sleeve member includes a leading edge and a trailing edge and wherein the driving means further includes a slot in the sleeve member on both the leading and trailing edges and wherein the threads on the sleeve member are adapted to cut in both the forward and reverse directions, enabling the sleeve member to be assembled onto the shaft with either end being the leading or trailing end.
9. The bone screw of claim 1 wherein the outside diameter of the second set of threads is greater than the outside diameter of the first set of threads.
10. The bone screw of claim 1 wherein the inner cylindrical surface of the sleeve member has a uniform diameter throughout providing an uninterrupted surface to directly slide against the smooth unthreaded portion of the shaft.

* * * * *